United States Patent
Wedel

(10) Patent No.: US 7,801,275 B2
(45) Date of Patent: Sep. 21, 2010

(54) IMAGING SYSTEM

(75) Inventor: Matthias Wedel, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 77 days.

(21) Appl. No.: 11/969,080

(22) Filed: Jan. 3, 2008

(65) Prior Publication Data

US 2008/0165927 A1 Jul. 10, 2008

(30) Foreign Application Priority Data

Jan. 5, 2007 (DE) .................... 10 2007 001 181

(51) Int. Cl.
*H05G 1/58* (2006.01)

(52) U.S. Cl. ..................... 378/98.9; 378/116

(58) Field of Classification Search .............. 378/62, 378/98.9, 98.11, 98.12, 114, 115, 116
See application file for complete search history.

(56) References Cited

U.S. PATENT DOCUMENTS

2008/0152075 A1* 6/2008 Paliwal et al. ............... 378/16

* cited by examiner

*Primary Examiner*—Chih-Cheng G Kao
(74) *Attorney, Agent, or Firm*—Brinks, Hofer, Gilson & Lione

(57) ABSTRACT

A medical imaging system is provided. The medical imaging system includes an imaging device with a radiation source and a detector, a control unit; and a processing unit. The processing unit is operable to compare a stored reference image taken using a high radiation dose with a current image taken using a lower radiation dose. The control unit is operable to trigger the imaging device to take a further image using a high radiation dose based on the comparison.

17 Claims, 1 Drawing Sheet

IMAGING SYSTEM

The present patent document claims the benefit of the filing date of DE 10 2007 001 181.6, filed Jan. 5, 2007, which is hereby incorporated by reference.

BACKGROUND

The present embodiments relate to an imaging system for capturing an image sequence.

During a number of medical applications (e.g. an endoscopic intervention), a patient is irradiated over a period of time for imaging purposes. The patient is continuously exposed to ionizing radiation during this time. During lengthy treatments, such continuous exposure results in radiation damage, such as reddening of the skin and other tissue damage. Medical personnel, such as the doctor carrying out the treatment and/or the medical personnel assisting the doctor may be in close proximity to the patient during the treatment. The medical personnel may be exposed to continuous stray radiation during the treatment.

Conventially, exposing the patient and the medical personnel to radiation in this way was regarded as acceptable in view of the medical benefit. Alternatively, the radiation dose was reduced, even though this adversely affects the image quality of the x-ray images obtained, as the image sharpness depends on the radiation dose. The radiation dose cannot therefore be reduced arbitrarily.

SUMMARY AND DESCRIPTION

The present embodiments may obviate one or more drawbacks or limitations inherent in the related art. For example, in one embodiment, patient imaging is performed in a non-damaging manner for capturing an image sequence over a period of time, the images obtained being characterized by high image quality.

In one embodiment, a method for capturing an image sequence includes taking a reference image using a high radiation dose of a radiation source; the references image is stored; taking another current image using a lower radiation dose; and comparing the reference image with the current image. If, on the basis of the comparison, a change is detected in the current image, another image is taken using a high radiation dose.

The method may used by a medical imaging device, such as an x-ray machine.

When capturing an image sequence, non-damaging imaging may be achieved by taking individual images using a high radiation dose instead of continuously applying a high radiation dose to the patient. This provides high-resolution (i.e. highly detailed) images that can be used as the comparison basis for detecting a movement or change in the patient's body. Such an image is, for example, the reference image which is followed by at least one current image that was taken using a lower radiation dose. The radiation dose of the current image is set such that the image quality is adequate for comparison with the reference image. A computer may automatically compare the reference image with the current image. The computer may detect dynamic processes resulting in a change in the current image compared to the older reference image. Only if such a change is detected will another image, which will replace the reference image, be taken using a high radiation dose. The replacement reference image will provide the medical personnel with an updated high-quality visualization of the processes in the patient's body. The imaging method may be used with a flat-panel x-ray machine and/or a computed tomography (CT) scanner.

The other image may not be a complete image, which reproduces the entire body region under examination depicted in the reference image. The other image may be a sub-area of the complete image. Only an image detail is captured with a high resolution. The image detail corresponds to the area of the current image in which the change was detected. The static areas are not continuously exposed to the full radiation, but only the areas in which changes are discernible are repeatedly captured using a high radiation dose.

The image detail may be inserted in the reference image at the position where the change was detected. This provides a complete current image with a high degree of sharpness, with only a small part of the patient's body having been exposed to the high radiation dose in order to update the reference image by the image detail. Suitable computer-based image processing techniques may be used to replace an image detail of the reference image by the image detail subsequently obtained.

The image made up of the image detail and the reference image may be stored as the updated reference image and used as the reference image for the comparison. The stored image may be used in an iterative loop. After detection of a movement or change by the current image, the reference image may be immediately adapted automatically so that a high-quality current recording of the body region under examination is available.

In one embodiment, to capture the image detail, a beam path of the medical imaging device is restricted by a collimator. The collimator may mask out part of the beam path, which reduces the radiation dose to which the patient is exposed. Using the part of the beam path passing through an aperture of the collimator, a high-quality recording of the region in which a change was detected in the current image can be obtained.

In one embodiment, the collimator may be moved automatically based on the change detected. The collimator may be set to image a plurality of details and positions. The method may be characterized by a particularly high degree of automation so that the method is carried out quickly.

The collimator may be moved to a number of predetermined positions. The number of predetermined positions is correlated with the size of the collimator aperture. Image details may be captured from all the predetermined positions, so that the contiguously disposed image details cover the entire image. For example, four defined collimator positions are provided which are matched to the size of the collimator aperture. The collimator may be moved to one of the four positions, so that one quadrant of the reference image may be taken in each case. Establishing the predefined positions enables the collimator to be controlled in a particularly simple manner.

In one embodiment, at least the reference image is visualized on a display. A high-resolution current image may be displayed in real time.

In one embodiment, the further image is taken if a predefined threshold value is exceeded when comparing the reference image with the current image. The threshold value represents a limit value of a visualization parameter, such as a predefined grayscale value, which visualization parameter is taken into account for comparing the reference image with the current image. The threshold value may be set by an imaging device operator. The sensitivity of a processing unit may be modified for evaluating the comparison result.

The radiation dose may be set using a control unit of the medical imaging device. The medical imaging device includes an x-ray generator for producing the beam path. The control unit of said x-ray generator automatically adjusts the intensity of the x-ray radiation, for example, the size of the radiation dose, based on the comparison of the reference image with the current image. Recordings with high or low image sharpness are accordingly obtained. The medical imaging device may be, for example, an x-ray emitter.

The current image may be taken with a radiation dose that may be less than 50% and, more preferably 25%, of the size of the radiation dose of the reference image. The radiation dose of the current image may be lower than the radiation dose of the reference image, however, it is sufficient for showing the relevant differences between the current image and the reference image in the specific application and using suitable methods. This may provide a particularly non-damaging patient imaging method in which the radiation dose for the patient is reduced.

In one embodiment, an imaging apparatus includes an imaging device with a radiation source and a detector, a control unit and a processing unit. The processing unit compares a stored reference image taken using a high radiation dose with a current image taken using a low radiation dose. The control unit triggers the imaging device to take another image with a high radiation dose on the basis of the comparison.

The components of the apparatus may be interconnected by a data link so that the imaging device is automatically triggered depending on the comparison result. The processing unit processes a software-based combination of mathematical and logical operations which enables the difference of the values of the visualization parameter (e.g. grayscale value) to be taken for each point of the reference image and of the current image, so that any exceedance of the predefined threshold value of the visualization parameter can be interpreted as a change. The processing unit may be part of the control unit, but can also constitute a separate entity connected to the control unit via a data link. If a change is detected, the control unit may automatically send a control signal to the imaging device to take the further image which will provide more precise information about the change than the current image.

In one embodiment, the imaging device may include a collimator that restricts a beam path of the radiation source when the further image is taken. The collimator may be adjusted automatically by the control device in order to obtain a recording of a particular image detail.

In one embodiment, the processing unit inserts the image detail into the reference image and stores the updated reference image.

BRIEF DESCRIPTION OF THE DRAWINGS

FIG. 2c shows a radiation dose and a dose-area product over time for the individual steps according to FIG. 2a.

DETAILED DESCRIPTION

Figure 1:
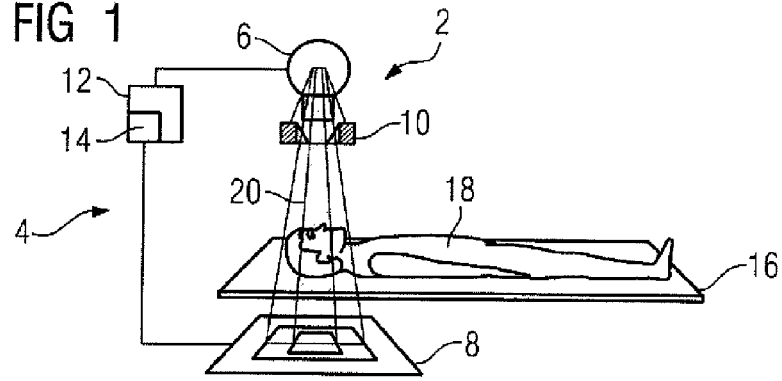
FIG. 1 schematically illustrates one embodiment of an imaging apparatus.

In one embodiment, as shown in FIG. 1, an imaging apparatus 2 includes an imaging device 4 with a radiation source 6, a radiation detector 8, and a collimator 10. The imaging device 4 may be an x-ray machine. The apparatus 2 may be controlled by a control unit 12 that includes a processing unit 14. A patient 18 positioned on a patient positioning table 16 may be moved into a beam path 20 emitted by a radiation source 6. A series of recordings of a region under examination of the patient 18 may be made using the imaging device 4. An image sequence may be recorded during a medical intervention with continuous irradiation of the patient 18.

Figure 2A:
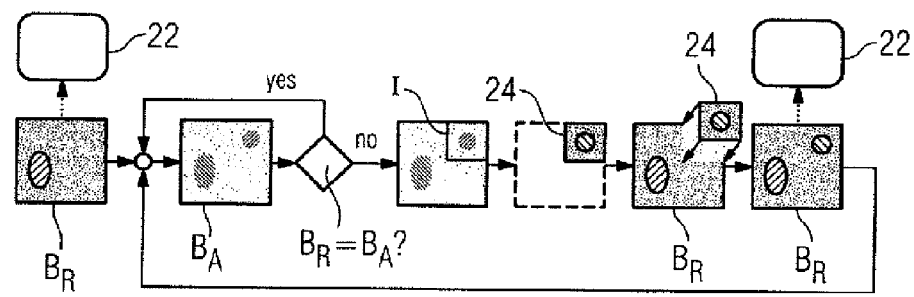
FIG. 2a shows a block diagram of a method for capturing an image sequence.

A method for capturing an image sequence is shown in the block diagram of FIG. 2a. A reference image $B_R$ with high image sharpness is taken with a high radiation dose $D_H$ (see FIG. 2c). The reference image $B_R$ may be stored and/or displayed on a display 22. The display 22 provides the treating physician with visual assistance during the medical intervention.

A series of current images $B_A$ of the entire region under examination may be taken. The current images $B_A$ may correspond to the reference image $B_R$ with respect to their size and position relative to the patient. A lower radiation dose $D_N$ is used. For example, the current images $B_A$ are less sharp. The processing unit 14 may automatically compare each of the current images $B_A$ with the reference image $B_R$ in respect of a visualization parameter, for example, the grayscale value of each image pixel. A predefined adjustable threshold value may be used for the comparison. If the two images coincide, for example, if the changes in the current image $B_A$ are below the threshold value, a further current image $B_A$ is taken. If changes exceeding the threshold value are detected in the current image $B_A$ compared to the reference image $B_R$, depending on the position of these changes, an image detail 24 is captured using a high radiation dose.

In the current image $B_A$ according to FIG. 2a, the changes are in a first quadrant I of the image $B_A$. The control unit 12 accordingly controls the collimator 10 to mask out part of the beam path 20. Only the first quadrant I is captured as an image detail 24. The size of an aperture 26 of the collimator 10 may be adjusted so that only a quarter of the total image, such as the first quadrant I, is captured. The image detail 24 is then automatically inserted into the reference image $B_R$, for example, at the position where the change was detected. For example, the image detail 24 is inserted in the first quadrant I of the reference image $B_R$. An updated reference image $B_R$ may be obtained, stored, and simultaneously displayed on the display 22. The updated reference image $B_R$ may be used as the basis for comparison with the subsequent current images $B_A$.

Figure 2B:
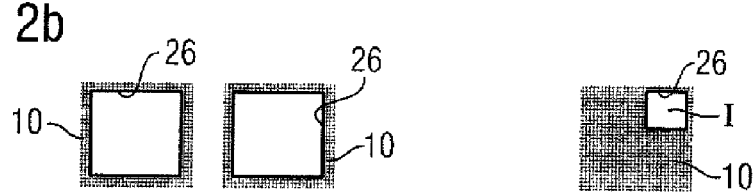
FIG. 2b schematically illustrates one embodiment of a collimator.
Figure 2C:
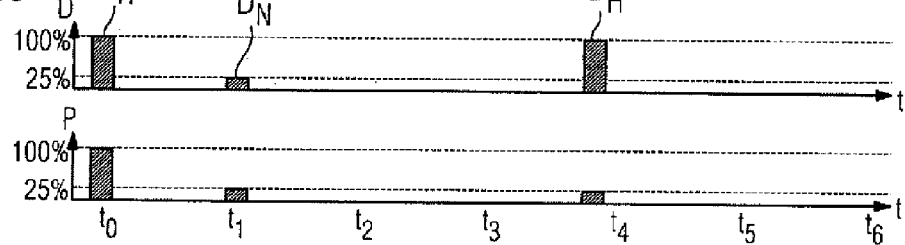

FIG. 2c shows a radiation dose D and a dose-area product P. FIG. 2c shows radiation dose per irradiated area over time t. The item instants $t_0$ to $t_6$ specify the times where the acts of the method are carried out. When the reference image $B_R$ is taken, a high radiation dose is used. The high radiation may be about 100% of the radiation dose D. The beam path 20 may remain unrestricted when the reference image $B_R$ and the current image $B_A$ are taken, so as to produce a maximally large-area complete image, as shown in FIG. 2b. As the reference image $B_R$ has a size which is defined as maximally large, the dose-area product P may remain 100%. When the current image $B_A$ is taken, a much lower radiation dose D is used. The lower radiation dose D may be about 25% of the maximum possible radiation dose $D_H$. The radiation dose D is regulated via an x-ray generator (not shown in greater detail here) of the x-ray device 4. The generator may be controlled via the control unit 12. The current image $B_A$ may be as large as the reference image $B_R$. The dose-area product P may be only about 25% based on the low radiation dose $D_N$.

In one embodiment, the collimator 10 is not used to screen off the beam path 20, apart from the first quadrant I in which a change was detected, until capture of the image detail 24 at time $t_4$. To capture the image detail 24, a maximum radiation dose $D_H$ is used. As the image area is restricted to a quarter of the total image area in this case, the dose-area product is only 25%. As shown in FIG. 2c, this method is particularly non-damaging for the patient, while at the same time the images displayed to assist the medical personnel have optimum image quality.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for imaging with a medical imaging device, the method comprising:
   obtaining a reference image using a high X-ray radiation dose of an X-ray radiation source;
   storing the reference image;
   obtaining a current image using a lower X-ray radiation dose;
   automatically comparing the reference image with the current image; and
   obtaining a further image using the high X-ray radiation dose when a change in the current image is detected based on the comparison of the reference image and the current image,
   wherein the lower X-ray radiation dose is lower than the high X-ray radiation dose.

2. The imaging method as claimed in claim 1, wherein obtaining the further image includes imaging an image detail using the high X-ray radiation dose, the image detail corresponding to an area of the current image in which the change was detected.

3. The imaging method as claimed in claim 2, comprising: inserting the image detail into the reference image at a position at which the change was detected.

4. The imaging method as claimed in claim 3, comprising: storing the image including the image detail and the reference image as the updated reference image.

5. The imaging method as claimed in claim 2, wherein a collimator restricts a beam path of the medical imaging device to capture the image detail.

6. The imaging method as claimed in claim 5, comprising: automatically moving the collimator to capture the image detail, movement based on the change detected.

7. The imaging method as claimed in claim 6, comprising: moving the collimator to a number of predefined positions.

8. The imaging method as claimed in claim 1, comprising: displaying at least the reference image on a display.

9. The imaging method as claimed in claim 1, comprising: obtaining the further image when comparison of the reference image with the current image reveals that a predefined threshold is exceeded.

10. The imaging method as claimed in claim 1, comprising: adjusting the X-ray radiation dose using a control unit of the medical imaging device.

11. The imaging method as claimed in claim 1, wherein obtaining the current image includes using an X-ray radiation dose less than 50% of the high X-ray radiation dose.

12. The imaging method as claimed in claim 11, wherein obtaining the current image includes using a X-ray radiation dose less than approximately 25% of the high X-ray radiation dose of the reference image.

13. The imaging method as claimed in claim 1, wherein obtaining is performed with an x-ray machine, and wherein the medical imaging device is an x-ray source.

14. An imaging system comprising:
   an imaging device with an X-ray radiation source and a detector;
   a control unit; and
   a processing unit operable to compare a stored reference image taken using a high X-ray radiation dose with a current image taken using a lower X-ray radiation dose,
   wherein the control unit is operable to trigger the imaging device to take a further image using the high X-ray radiation dose based on the comparison, and
   wherein the lower X-ray radiation dose is lower than the high X-ray radiation dose.

15. The imaging apparatus as claimed in claim 14, wherein the imaging device is operable to obtain an image detail using a collimator that restricts a beam path of the X-ray radiation source for taking the further image.

16. The imaging apparatus as claimed in claim 15, wherein the processing unit is operable to insert the image detail into the reference image and to store as the updated reference image.

17. A method for capturing an image sequence with an x-ray device, the method comprising:
   obtaining a reference image using a high X-ray radiation dose and a current image using a lower X-ray radiation dose;
   comparing the reference image with the current image; and
   imaging a further image using the high X-ray radiation dose when a difference in one or more areas of the current image is detected based on the comparison of the reference image and the current image,
   wherein the lower X-ray radiation dose is lower than the high X-ray radiation dose.

* * * * *